(12) United States Patent
Anselmi et al.

(10) Patent No.: US 10,744,081 B2
(45) Date of Patent: Aug. 18, 2020

(54) NATURAL-BASED MASCARA WITH HIGH COSMETIC EFFECT

(71) Applicant: Prodotti Gianni S.r.l., Milan (IT)

(72) Inventors: Cecilia Anselmi, Siena (IT); Marisanna Centini, San Quirico d'Orcia (IT); Cristina Silverio, Padula (IT); Maria Francesca Tola, Partinico (IT)

(73) Assignee: PRODOTTI GIANNI S.R.L., Milan (IT)

( * ) Notice: Subject to any disclaimer, the term of this patent is extended or adjusted under 35 U.S.C. 154(b) by 0 days.

(21) Appl. No.: 16/043,804

(22) Filed: Jul. 24, 2018

(65) Prior Publication Data

US 2020/0030224 A1   Jan. 30, 2020

(51) Int. Cl.
*A61K 8/9789* (2017.01)
*A61Q 1/10* (2006.01)
*A61K 8/9794* (2017.01)
*A61K 8/98* (2006.01)
*A61K 8/34* (2006.01)
*A61K 8/92* (2006.01)
*A61K 8/49* (2006.01)
*A61K 8/55* (2006.01)
*A61K 8/29* (2006.01)
*A61K 8/73* (2006.01)
*A61K 8/37* (2006.01)

(52) U.S. Cl.
CPC .............. *A61K 8/9789* (2017.08); *A61K 8/29* (2013.01); *A61K 8/345* (2013.01); *A61K 8/347* (2013.01); *A61K 8/37* (2013.01); *A61K 8/498* (2013.01); *A61K 8/55* (2013.01); *A61K 8/732* (2013.01); *A61K 8/922* (2013.01); *A61K 8/9794* (2017.08); *A61K 8/988* (2013.01); *A61Q 1/10* (2013.01); *A61K 2800/43* (2013.01)

(58) Field of Classification Search
None
See application file for complete search history.

(56) References Cited

U.S. PATENT DOCUMENTS

| 8,846,018 B2 | 9/2014 | Atis et al. |
| 2004/0219124 A1 | 11/2004 | Gupta |
| 2013/0164241 A1 | 6/2013 | Foley et al. |
| 2015/0297473 A1 | 10/2015 | Fave Bekisz et al. |

FOREIGN PATENT DOCUMENTS

| CN | 103893097 A | 7/2014 |
| FR | 2984124 A1 | 6/2013 |
| JP | 2002308735 A | 10/2002 |
| KR | 20000026081 A | 5/2000 |
| WO | 2011158161 A2 | 12/2011 |
| WO | 2012012084 A2 | 1/2012 |
| WO | 2013007599 A2 | 1/2013 |
| WO | 2014105733 A1 | 7/2014 |

OTHER PUBLICATIONS

English translation of JP2002308735 retrieved from Espacenet on Sep. 16, 2019.*
Neal's Yard Remedies retrieved from http://www.gnpd.com (Year: 2014).*

\* cited by examiner

*Primary Examiner* — Jessica Worsham
(74) *Attorney, Agent, or Firm* — Lucas & Mercanti, LLP

(57) ABSTRACT

A natural-based mascara composition containing psyllium fibers mixed with other vegetable fibers, free of synthetic polymers and synthetic fibers, with optimal volumizing, elongation and adhesiveness to eyelashes characteristics is disclosed. The psyllium fibers and other vegetable fibers are present as a whole in a weight percentage from 1 to 10% on the weight of the mascara. The mascara further contains by weight on the weight of the mascara: 1-10% emulsifiers, 2-20% oils, 3-25% waxes, and 1-10% dyes.

5 Claims, 3 Drawing Sheets

A

B

A

B

NATURAL-BASED MASCARA WITH HIGH COSMETIC EFFECT

FIELD OF THE INVENTION

The present invention belongs to the field of research and development of high-performing natural cosmetic products. New eye make-up compositions comprising a particular combination of natural fibers associated with emulsifiers and other ingredients known in the art are described. The resulting products show a high eyelashes volumizing and elongation effect, avoiding commonly used synthetic film-forming polymers.

BACKGROUND OF THE INVENTION

Mascara is a cosmetic product for application to eyelashes: the main cosmetic effects required for this type of product are the volume increase (volumizing), eyelashes elongation and curling; mascaras must also have characteristics useful for their application, i.e. sufficient fluidity, spreadability, adhesiveness to the eyelashes, absence of lumps, easy spreadability during make-up removal, etc.; these characteristics are not always easy to combine with eyelash thickening/elongation/curling cosmetic effects.

Mascaras are generally based on emulsifying systems associated with oils, waxes or lipophilic substances, to obtain a sufficiently fluid base; they are associated with polymeric and/or fibrous products useful to afford consistency and obtain eyelashes thickening/elongation, as well as dyes to confer color; the use of film-forming agents promoting product adhesion and uniform eyelashes coverage is also widespread.

In the field there are numerous publications and patents, often focused on specific mascara ingredients and/or combinations thereof. For example, two patent publications FR2984124 and WO2013007599, relate to an emulsifying system that ensures emulsion stability in order to obtain a mascara characterized by a thick texture allowing a homogeneous volumizing deposit on the eyelashes.

Patent application CN103893097 refers to liquid or solvent-type (waterproof) mascaras with properties of easy removal ("caring properties"); they obtain an eyelashes lengthening effect by use of various types of polymers, combination of synthetic fibers and film-forming agents or polymer-coated synthetic fibers.

The "curling" effect has been highlighted, for example, in patent application WO2011158161, by the use of retractable fibers based on polyethylene terephthalates which change length and shape in response to an external stimulus.

Patent application WO2014105733 shows an improvement in properties such as thickness, length, curling, better separation of eyelashes, resistance to spreading or formation of clots and easy removal by using at least one film-forming polymer, at least one silicone elastomer and at least one wax.

Patent application US2013/0164241 shows "primer" formulations and mascara formulations giving a lengthening and thickening effect (thick eyelashes), easy to remove and with no damages to the eyelashes; the "primer", based on synthetic polymers, is applied directly on the eyelashes and dries quickly: this allows users to apply a second mascara formulation where the primer has been applied, creating the requested substantivity for the second application consisting of mascara; also the "primer" formulation is easily washed out from the eyelashes, resulting in easy removability of the second mascara formulation; this mascara contains a mixture of synthetic fibers in combination with synthetic and natural film-forming compound which retain fibers in situ and extend the eyelashes.

Korean patent application KR200026081 uses hemp and bamboo cellulose in combination with synthetic film-forming agents (alkyl acrylate copolymers).

Long and thick eyelashes are also obtained with the mascara described in patent application JP2002308735: this product contains cotton, linen, silk fibers associated with an emulsion of acrylic copolymers.

WO2012/012084 describes naturally-derived mascara compositions with a fixative system comprising a natural polymeric film-forming system comprising pullulan and candelilla wax resin, and a natural plasticizer rosin and a sebacic acid/castor oil copolymer, such ingredients being taught as responsible for obtaining lengthening and volumizing effects; various excipients, inter alia fiber materials, can be optionally added to the composition to the extent that they do not interfere.

US2004/0219124 exemplifies a non-emulsified, oil/wax-free facial mask composition including inter alia polyethylene glycol and psyllium husk powder; the mask, further including facial slimming ingredients and antioxidants, has the property of being peeled-off in one piece as a consistent film.

US2015/0297473 exemplifies acrylates-based mascara compositions forming a lamellar phase; the description mentions a list of optional ingredients, e.g. thickeners, among which Psyllium husks powder is generally mentioned.

In this field the use of synthetic film-forming polymers such as e.g. polyacrylates, polyurethanes, polyamides, polyolefins, silicones and their polymers, polyesters, polyacetates, etc. is very common; such products are increasingly less desirable by consumers, both in view of possible incorporation of toxic residues deriving from synthesis process, and for the growing trend in preferring natural products having low impact on the human body and environment. However, it is difficult avoiding the use of those products as they are essential in promoting high adhesion and uniform eyelashes coverage, such that the tendency to reduce the "synthetic" mascara component is often accompanied by a reduction in performance, e.g. in terms of adhesiveness or coating homogeneity. The present invention addresses and solves these problems, providing a new natural-based mascara, with a simple and effective composition, which avoids the use of synthetic polymers, having performance characteristics equal or even higher than those of the products commonly in use.

SUMMARY OF THE INVENTION

One object of the present invention is to provide a new composition for eye make-up, specifically for mascara, comprising psyllium fibers mixed with further natural vegetable fibers. The composition does not require the use of synthetic polymers and synthetic fibers, and has optimal eyelashes volumizing, elongation and adhesiveness characteristics. The invention also includes a method of producing said mascara and its use in the cosmetic field.

DETAILED DESCRIPTION OF THE INVENTION

Figure 1:
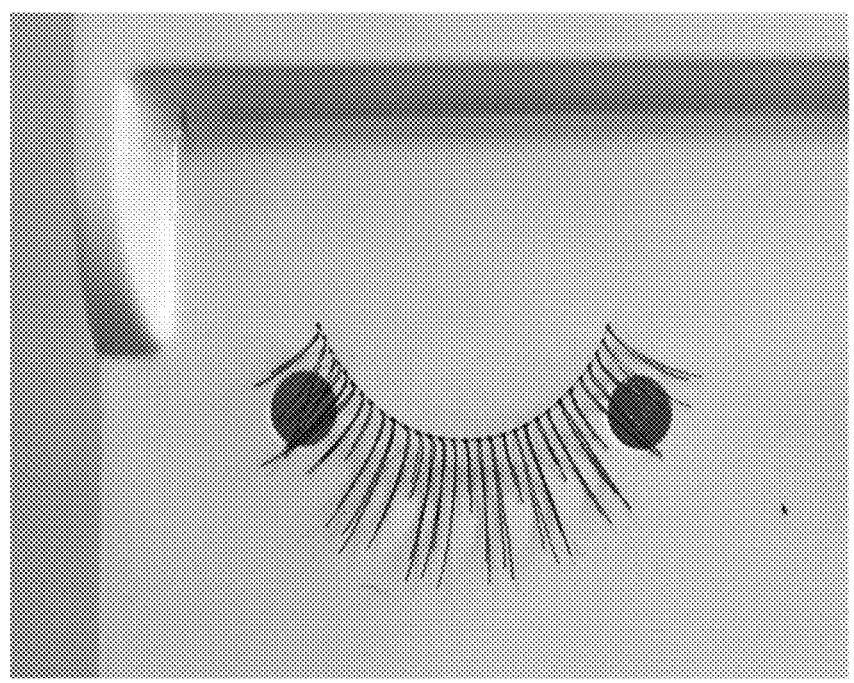
FIG. 1: artificial eyelashes (substrate) used for evaluation of effects of the compositions of the invention.

The main object of the invention is a natural-based mascara comprising fibers, wherein said fibers consist in psyllium fibers and other vegetable fibers.

Herein, "mascara" means, as commonly known in the art, a product suitable for application to eyelashes and for temporary coating thereof, comprising characteristic mascara ingredients such as emulsifiers, fibers, oils, waxes and pigments. *The Collins English Dictionary* defines mascara as, "a cosmetic substance for darkening, lengthening, curling, colouring, and thickening the eyelashes, applied with a brush or rod". Mascaras are classified as aqueous mascaras or waterproof mascaras. The present application relates to aqueous mascaras: they are characterized by containing a vehicle being an oil-in-water emulsion, in which oils and waxes are emulsified in water; by contrast, waterproof mascaras contain oils/waxes dispersed in organic solvents.

In the definition of mascara, the term "natural-based" used herein identifies a mascara exempt from any synthetic polymers (for example acrylic polymers or copolymers (e.g., acrylates, methacrylates, alkyl acrylates, alkyl methacrylates, polyacrylates, polymethacrylates), polyolefins, polyglycols, polyvinyls, polyurethanes, polyamides, polyimides, polyethers, polyesters, fluoropolymers, polyethers, polyacetates, polycarbonates, epoxides, aldehyde resins, polysiloxanes, polyquaterniums, etc.); the term "natural-based" allows the use of natural polymers or natural-derived polymers, i.e. chemically-modified natural polymers.

As indicated above, in the mascara which is object of the invention, the fiber component comprises exclusively vegetable fibers, and among them specifically psyllium fibers. The psyllium fibers, deriving from plants of *Plantago* genus, in particular *Plantago* psyllium, are per se well known, commercially available (for example from Kadamexports or Jyotindra International) and generally used as food supplements. Preferably they have average length below 200 µm, more preferably below 150 µm (i.e. more than 95% of the fibers pass through 200 or 150 µm sieve, respectively).

In the present invention, psyllium fibers are used in synergistic association with other plant fibers. These other fibers are synthetically referred herein as "associated fibers": they can be widely selected from the group of known vegetable fibers; among them citrus, agave, pineapple, oat, bamboo, beet, cocoa, cactus, hemp, artichoke, carrot, cellulose, chicory, wheat, corn, apple, barley, potato, pea, tomato, rice, etc. and their mixtures can be mentioned; the combination of psyllium and bamboo fibers is herein preferred. Vegetable fibers are widely available commercially; e.g., bamboo fibers are distributed e.g. from Creafill Fibers Corp. Preferably the associated fibers used herein have an average length between 0.1 and 500 µm, more preferably 10 and 180 µm in particular between 20 and 150 µm, e.g. 30, 60, 115, 130 µm. Preferably, the associated fibers have a wide length distribution within the aforementioned ranges: this result can be obtained, for example, with a mix of three types of fibers, having average lengths of 30, 60 and 115 µm, respectively.

All the fibers used herein (i.e. psyllium and associated fibers) have exclusively vegetable origin, i.e. they are "natural" fibers. The use of artificial fibers is not provided. The weight percentage of the combination of said fibers (psyllium+associated fibers) is generally between 1 and 10% on the weight of the final mascara, preferably between 1.5% and 7%, e.g. 2,3,4,5,6,7%. Compared to the total number of used fibers (psyllium+associated fibers), the weight percentage of psyllium fibers is preferably between 1 and 20%, more preferably between 3 and 10%, e.g. 6%.

In addition to the aforementioned ingredients, the present composition contains ingredients commonly required in the mascara sector: without limitation, the following classes can be mentioned: emulsifiers, waxes, oils, dyes, preservatives, antioxidants, generally in an aqueous vehicle may be mentioned; synthetic film-forming polymers are not necessary, as this function is effectively performed by the mixture of fibers used herein; therefore the composition may be free from such agents.

The emulsifiers are generally used in a weight percentage from 1 to 10%, based on the weight of mascara, and can be widely chosen among those commercially available. Non-limiting examples are: potassium cetyl phosphate, or glyceryl stearate citrate; particularly preferred emulsifiers within the meaning of the invention are those comprising starch, e.g. the Emulprogress EC2 product distributed by Prodotti Gianni S.p.A.

Oils are generally used in a weight percentage between 2 and 20% based on the weight of mascara, and can be widely selected among those commercially available; examples of oils are: caprylic/capric acid triglycerides, tricapriline, isoamyl laurate, vegetable oils, such as: castor, sesame, flax, coconut, corn, cotton seed, olive, palm, illipé, rapeseed, soybean, sunflower, walnut, avocado, camellia, macadamia nut, grape seed, peanut, jojoba oils, etc.

Waxes are generally used in a weight percentage between 3 and 25% based on the weight of mascara, and can be widely selected from those commercially available. Non-limiting examples are: beeswax, spermaceti, lanolin, shellac wax, carnauba wax, candelilla wax, sugar cane wax, rice wax, olive wax. Among the favourite ones, carnauba wax and beeswax are to be mentioned.

Dyes can be chosen preferably among minerals or organic pigments. The pigments can be white or colored, and/or pearly. Among the mineral pigments, titanium dioxide, coated titanium dioxide, iron oxides, chromium, manganese violet, ultramarine blue, etc. can be mentioned. Among the organic pigments, the carbon black and those allowed by the regulation (CE) 1223/2009 for the ocular zone can be mentioned. Examples of white pearly pigments are titanium dioxide- or bismuth oxychloride-coated mica. An example of colored pigment is mica with titanium dioxide, iron oxides, etc. Dyes are generally used in a weight percentage between 1 and 10% based on the weight of mascara, Preservatives and antioxidants, according to the invention, can be selected from those available and accepted in products with a "natural" connotation, generally used in a weight percentage variable according to known quantities depending on the specific preservative. Non-limiting examples of preservatives and antioxidants are benzoic acid, sorbic acid, dehydroacetic acid, benzyl alcohol, anisic acid, tocopherol and derivatives, tocopherol-based mixtures, etc.

Further possible ingredients are, without limitation: consistency factors, in proportions preferably ranging from 1 to 10% by weight on mascara (e.g. glyceryl behenate, glyceryl stearate), additives with "caring" effect, perfumes, emollients, sequestrants, neutralizing agents, sunscreens, lacquers, fillers, rheological modifiers, stabilizers, pH correctors, humectants (e.g. glycerin), moisturizers, vitamins, hyaluronic acid, etc.

The carrier is an aqueous solvent, preferably water, present as an oil-in-water emulsion in which the lipohilic components of the composition are emulsified.

An important feature of the mascaras of the present invention is the absence of any synthetic polymer (such ingredients are widely used in mascaras, in particular as film-forming agents); the present fiber combination resulted able to give excellent adhesiveness and coating homogeneity characteristics to the mascara, making the use of such agents superfluous; advantageously, the absence of synthetic polymers increases product pleasantness and, above all, avoids exposing the user to traces of by-products deriving from polymerization processes; in this way a more "safe" cosmetic product, with lesser impact on the user and the environment is obtained. The synthetic polymers not present in the mascara of the invention are typically, but not exclusively, those used as film-forming and are represented, without limitation, by: acrylic polymers or copolymers (e.g., acrylates, methacrylates, alkyl acrylates, alkyl methacrylates, polyacrylates, polymethacrylates), polyolefins, polyvinyls, polyurethanes, polyamides, polyimides, polyethers, polyesters, fluoropolymers, polyethers, polyacetates, polycarbonates, rubbers, epoxides, aldehyde resins, polysiloxanes, polyquaterniums and the like.

A further important feature of the mascaras of the present invention, resulting from the aforementioned selection of fibers, is the absence of any synthetic fiber. e.g. nylon, rayon, etc. The present combination of natural vegetable fibers was indeed found suitable for obtaining the effects described herein, without using synthetic fibers.

The invention further comprises a process for the preparation of a mascara as described above, comprising preparing a mixture of ingredients for mascara comprising fibers, wherein said fibers consist of psyllium fibers and other vegetable fibers, as previously described.

The invention further comprises the use of a mascara as described above in the cosmetic field, or as an eye product, in particular for eyelash and/or eyebrow coating, with a make-up and protective effect, as it is free from synthetic polymers and synthetic fibers. The use of the natural fiber mixture described above allows achieving the required effects in a mascara in an optimal way: increasing the eyelashes volume and length with a smudge-free effect, with a good separation among eyelashes and an excellent eyelashes curling. The extending and volumizing effect is comparable or superior to that obtainable from mascara containing polymers and synthetic fibers. In particular, as shown in the examples, a composition according to the invention comprising psyllium and bamboo fibers improves curling, separation, length, thickness, resistance to spreading. The mascaras of the invention are also easy to remove and do not damage the eyelashes.

Experimental Examples

In the non-limiting examples shown below, mascara formulations according to the invention are shown, unless otherwise indicated. The effect obtained by application on standard artificial eyelashes is also shown. All the compositions according to the invention showed clear eyelashes elongation and volumization properties and an evident film-forming effect; in the formulations including the EC2 emulsifier, these effects were further increased.

According to example 1, the emulsifier is Emulprogress EC2. The wax mixture consists of beeswax and carnauba wax. Consistency factors are glyceryl monostearate and glyceryl behenate. Vegetable oils are castor oil and caprylic/capric acid triglyceride. The pigment is titanium dioxide plus colored pigments. Tocopherol and Euxyl k900 represent the preservative and antioxidant system. The psyllium+ bamboo fiber mixture is present at 5%.

| EXAMPLE 1 | |
|---|---|
| Emulprogress EC2 | 3 |
| Glycerin | 4 |
| Glyceryl Stearate | 1.5 |
| Beeswax Alba Wax | 6 |
| *Copernicia Cerifera* (Carnauba) Wax | 3 |
| Caprylic/Capric Triglyceride | 6.5 |
| Aqua | q.s. to 100 |
| Isoamyl laurate | 2.5 |
| *Ricinus communis* seed oil | 1 |
| Pigments * | 5.5 |
| Benzyl Alcohol (and) Ethylhexylglycerin (and) Tocopherol | 1 |
| Tocopherol | 1 |
| Glyceryl behenate | 3 |
| Mixture of psyllium + bamboo fibers | 5 |

* white and colored pH 6.98

| EXAMPLE 2 (Reference) | |
|---|---|
| Emulprogress EC2 | 3 |
| Glycerin | 4 |
| Glyceryl Stearate | 1.5 |
| Beeswax Alba Wax | 6 |
| *Copernicia Cerifera* (Carnauba) Wax | 3 |
| Caprylic/Capric Triglyceride | 6.5 |
| Aqua | q.s. to 100 |
| Isoamyl Laurate | 2.5 |
| *Ricinus communis* seed oil | 1 |
| Pigments * | 5.5 |
| Benzyl Alcohol (and) Ethylhexylglycerin (and) Tocopherol | 1 |
| Tocopherol | 1 |
| Glyceryl behenate | 3 |
| pH = 7.01 | |

* white and colored

Figure 2:
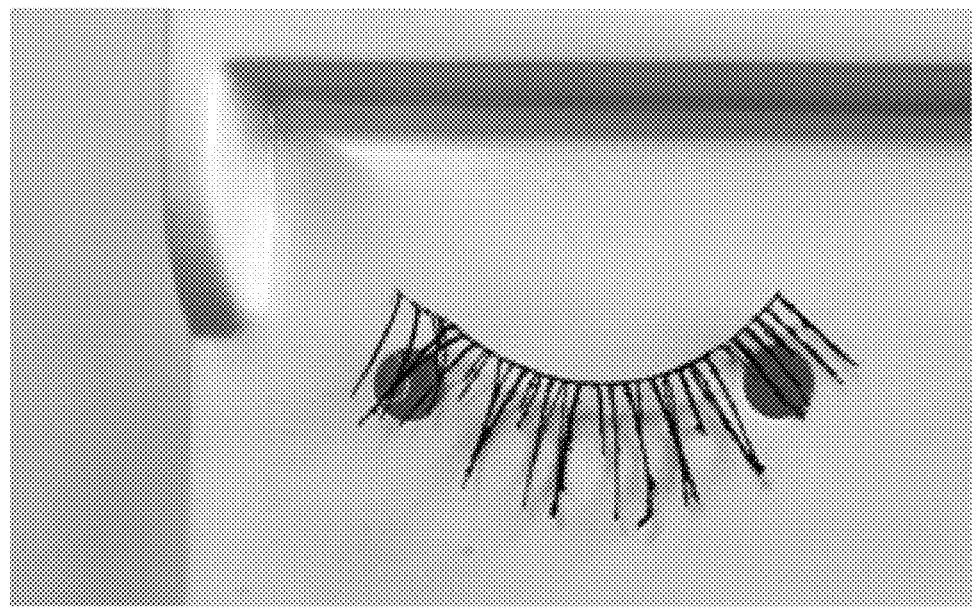
FIG. 2: coating effect on artificial eyelashes obtained by compositions of the invention according to: (A) Example 1; (B) Example 5.
Figure 2:
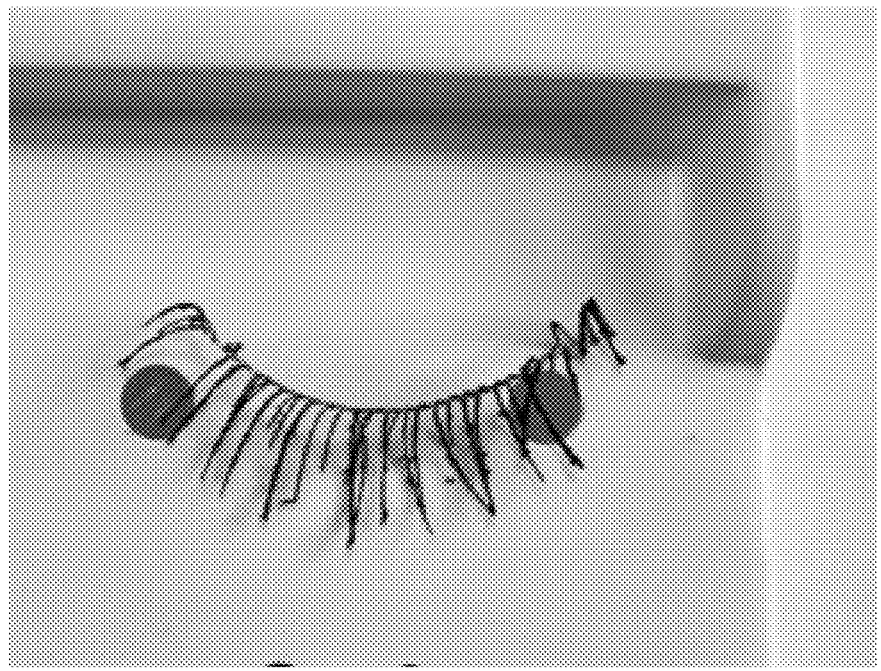

According to the reference example 2 the base is free of fibers, as reported. As shown in FIG. 2A, the product prepared according to Example 1 was found readily applicable on both natural and artificial eyelashes and reapplied as desired. It has the following effects: thick, longer eyelashes, curving effect, long-lasting, free of lumps, not spread out. The product prepared according to the reference example 2 (FIG. 3A) is easily applicable, has a "clean" effect but is less volumizing and lengthening.

| EXAMPLE 3 | |
|---|---|
| Potassium Cetyl Phosphate | 1.5 |

EXAMPLE 3

| | |
|---|---|
| Glycerin | 4 |
| Glyceryl Stearate | 4 |
| Beeswax Alba Wax | 6 |
| *Copernicia Cerifera* (Carnauba) Wax | 3 |
| Caprylic/Capric Triglyceride | 6.5 |
| Aqua | q.s. to 100 |
| Isoamyl laurate | 2.5 |
| *Ricinus communis* seed oil | 1 |
| Pigments* | 5.5 |
| Benzyl Alcohol (and) Ethylhexylglycerin (and) Tocopherol | 1 |
| Tocopherol | 1 |
| Glyceryl behenate | 3 |
| Mixture of psyllium + bamboo fibers | 4.5 |
| pH = 7.36 | |

*white and colored

EXAMPLE 4

| | |
|---|---|
| Glyceryl Stearate Citrate | 4 |
| Glycerin | 4 |
| Glyceryl Stearate | 4 |
| Beeswax Alba Wax | 6 |
| *Copernicia Cerifera* (Carnauba) Wax | 3 |
| Caprylic/Capric Triglyceride | 6.5 |
| Aqua | q.s. to 100 |
| Isoamyl laurate | 2.5 |
| *Ricinus communis* seed oil | 1 |
| Pigments * | 5.5 |
| Benzyl Alcohol (and) Ethylhexylglycerin (and) Tocopherol | 1 |
| Tocopherol | 1 |
| Glyceryl behenate | 3 |
| Mixture of psyllium + bamboo fibers | 5 |
| pH = 7.40 | |

*white and colored

EXAMPLE 5

| | |
|---|---|
| Emulprogress EC2 | 3 |
| Glycerin | 3 |
| Glyceryl Stearate | 2.5 |
| Beeswax Alba Wax | 6.5 |
| *Copernicia Cerifera* (Carnauba) Wax | 2 |
| Caprylic/Capric Triglyceride | 5 |
| Aqua | q.s. to 100 |
| Hydrogenated Vegetable Oil | 6.5 |
| Hydrogenated Stearyl Olive Oil Esters | 1.7 |
| Hydrogenated Decyl Olive Oil Esters | 0.4 |
| Pigments * | 5 |
| Benzyl Alcohol, Ethylhexylglycerin, Tocopherol | 1 |
| Tocopherol | 0.5 |
| Cocoglycerides | 1.7 |
| *Ricinus communis* seed oil | 1.7 |
| Mixture of psyllium + bamboo fibers | 2 |
| *Linum usitatissimum* oil | 0.4 |
| *Sesamum Indicum* Oil | 0.4 |
| Sodium Hyaluronate | 0.2 |
| pH = 7.40 | |

* white and colored

Figure 3:
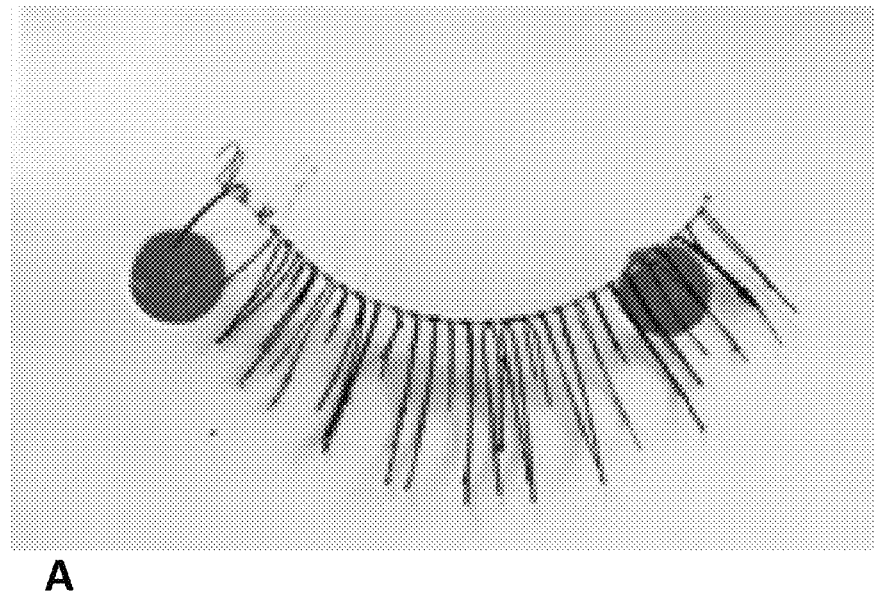
FIG. 3: coating effect on artificial eyelashes obtained by: (A) the reference composition according to Example 2; (B) the composition of the invention according to Example 3.
Figure 3:
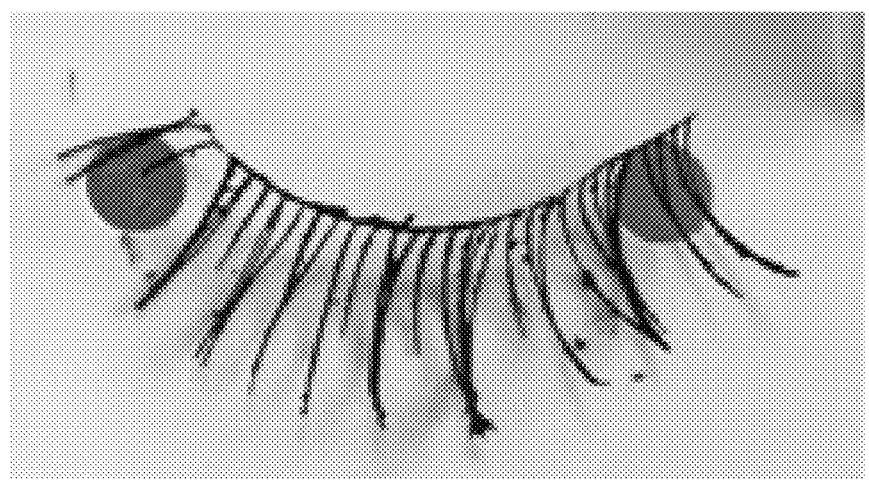

As evident from FIGS. 2B and 3B, the examples made according to the invention have effects similar to those of example 1.

In summary, in all the examples of the invention reported above, the product can be easily spread on eyelashes, with a drying time suitable for subsequent application of the product without creating lumps, furthermore it does not require a "primer" to be applied but creates the requested substantivity for subsequent applications. The compositions shown do not damage the eyelashes and are easily removed. A "clean" effect without clumping, with well-separated eyelashes, is also obtained.

The invention claimed is:

1. Natural-based mascara comprising fibers, wherein said fibers consist of psyllium fibers and other vegetable fibers present as a whole in a weight percentage from 1.5 to 7% on the weight of the mascara,
said mascara further comprising, by weight on the weight of the mascara: 1-10% emulsifiers, 2-20% oils, 3-25% waxes, and 1-10% dyes,
wherein said mascara is free of synthetic polymers, said psyllium fibers being present in a weight percent of from 1 to 20% of said psyllium fibers and other vegetable fibers as a whole, and said other vegetable fibers having an average length of from 10 to 180 µm.

2. Mascara according to claim 1, wherein said psyllium fibers are present in a weight percent of from 3 to 10% of said psyllium fibers and other vegetable fibers as a whole.

3. Mascara according to claim 1, wherein said other vegetable fibers are selected from the group consisting of: citrus, agave, pineapple, oats, bamboo, beetroot, cocoa, cactus, hemp, artichoke, carrot, cellulose, chicory, wheat, corn, apple, barley, potato, tomato, pea, rice and mixtures thereof.

4. Mascara according to claim 1, wherein said emulsifiers are starch-containing emulsifiers.

5. Process for the preparation of a mascara of claim 1, comprising preparing a mixture of: fibers, wherein said fibers consist of psyllium fibers and other vegetable fibers present as a whole in a weight percentage from 1.5 to 7% on the weight of the mixture, the mixture further comprising, by weight on the weight of the mixture: 1-10% emulsifiers, 2-20% oils, 3-25% waxes, and 1-10% dyes.

* * * * *